United States Patent
Sugimoto

(10) Patent No.: US 9,738,578 B2
(45) Date of Patent: Aug. 22, 2017

(54) METHOD FOR PRODUCING FLUORINATED HYDROCARBON

(71) Applicant: ZEON CORPORATION, Tokyo (JP)

(72) Inventor: Tatsuya Sugimoto, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 15/116,088

(22) PCT Filed: Feb. 9, 2015

(86) PCT No.: PCT/JP2015/053537
§ 371 (c)(1),
(2) Date: Aug. 2, 2016

(87) PCT Pub. No.: WO2015/122386
PCT Pub. Date: Aug. 20, 2015

(65) Prior Publication Data
US 2017/0174588 A1      Jun. 22, 2017

(30) Foreign Application Priority Data

Feb. 12, 2014   (JP) .................................. 2014-024501

(51) Int. Cl.
*C07C 17/361*   (2006.01)
*B01J 31/14*    (2006.01)

(52) U.S. Cl.
CPC .......... *C07C 17/361* (2013.01); *B01J 31/146* (2013.01); *B01J 2231/42* (2013.01)

(58) Field of Classification Search
CPC .... C07C 17/361; B01J 31/146; B01J 2231/42
See application file for complete search history.

(56) References Cited

U.S. PATENT DOCUMENTS

| 2,550,953 | A  | 5/1951 | Barrick et al. |
|---|---|---|---|
| 5,780,672 | A  | 7/1998 | Pasenok et al. |
| 2011/0068086 | A1 | 3/2011 | Suzuki et al. |
| 2016/0016869 | A1 | 1/2016 | Sugimoto |

FOREIGN PATENT DOCUMENTS

| JP | 59-46251 A     | 3/1984  |
|---|---|---|
| JP | 9-048741 A     | 2/1997  |
| JP | 2009-292749 A  | 12/2009 |
| WO | 2009/123038 A1 | 10/2009 |
| WO | 2014/136877 A1 | 9/2014  |

OTHER PUBLICATIONS

Translation of Written Opinion dated Mar. 31, 2015, issued in International Application No. PCT/JP2015/053537. (5 pages).
International Search Report dated Mar. 31, 2015, issued in counterpart International Application No. PCT/JP2015/053537 (2 pages).
Suzuki et al., "An Acid-catalyzed Reaction of Methyl Ethers with Acetyl Fluoride. Syntheses of 1-Fluorobicyclo[2.2.2] octanes", Bulletin of the Chemical Society of Japan, 1968, vol. 41, No. 7, pp. 1724-1725.
Kimura et al.,"Alkylation of Butyl Alcohols by Dialkyl Sulfates Using Phase Transfer Catalysis", Journal of the Japan Oil Chemist's Society, vol. 31, 1982, pp. 960-962.
Norris et al., "The Reactivity of Atoms and Groups in Organic Compounds. XII. The Preparation and Properties of Mixed Aliphatic Ethers With Special Reference to Those Containing the Tert.-Butyl Radical", Journal of American Chemical Society, vol. 54, 1932, pp. 2088-2100.
Clark et al., "Reactions of Potassium Fluoride in Glacial Acetic Acid with Chlorocarboxylic Acids, Amides, and Chlorides. The Effect of Very Strong Hydrogen Bonding on the Nucleophilicity of the Fluoride Anion", Journal of Chemical Society Dalton Translation,1975, pp. 2129-2134.
Calloway, "Reactions in the Presence of Metallic Halides. II. The Behavior of Fluorides and the Reactivity of the Halogens", Journal of American Chemical Society, vol. 59, 1937, pp. 1474-1479.

*Primary Examiner* — Jafar Parsa
(74) *Attorney, Agent, or Firm* — Westerman, Hattori, Daniels & Adrian, LLP

(57) ABSTRACT

The present invention is a method for producing a fluorohydrocarbon represented by a structural formula (3) comprising bringing a secondary or tertiary ether compound represented by a structural formula (1) into contact with an acid fluoride represented by a structural formula (2) in a hydrocarbon-based solvent in the presence of a boron trifluoride complex. (In structural formulae (1) to (3), each of $R^1$ and $R^2$ represents an alkyl group having 1 to 3 carbon atoms, $R^3$ represents a hydrogen atom, a methyl group, or an ethyl group, and each of $R^4$ and $R^5$ represents a methyl group or an ethyl group, provided that $R^1$ and $R^2$ are optionally bonded to each other to form a ring structure.)

$$\underset{(1)}{\overset{R^2}{\underset{R^3}{R^1-C-OR^4}}} + \underset{(2)}{R^5-COF} \xrightarrow{\text{Boron trifluoride complex}} \underset{(3)}{\overset{R^2}{\underset{R^3}{R^1-C-F}}}$$

5 Claims, No Drawings

METHOD FOR PRODUCING FLUORINATED HYDROCARBON

TECHNICAL FIELD

The present invention relates to a method for producing a fluorohydrocarbon that is useful as a plasma reaction gas (e.g., a plasma reaction gas for etching or chemical vapor deposition (CVD)) used in the field of production of a semiconductor device, a fluorine-containing drug intermediate, and a hydrofluorocarbon-based solvent. A high-purity fluorohydrocarbon thus produced is particularly suitable as a plasma etching gas, a CVD gas, and the like that are used in the field of production of a semiconductor device that utilizes a plasma reaction.

BACKGROUND ART

In recent years, semiconductor production technology that achieves further miniaturization has been developed, and a line width of 20 nm or 10 mm has been used for a leading-edge process. The degree of difficulty in processing has increased along with an increase in the degree of miniaturization, and various techniques are currently under development using various approaches (e.g., materials, devices, and processing methods).

In view of the above situation, the applicant of the present application developed a dry etching gas that can deal with a leading-edge dry etching process, and found that a saturated fluorohydrocarbon having a small number of fluorine atoms exhibits performance better than that of monofluoromethane that is widely used for etching a silicon nitride film (see Patent Literature 1).

Several methods have been known as a method for producing 2-fluorobutane. For example. Patent Literature 2 discloses a method that brings N,N'-diethyl-3-oxomethyltrifluoropropylamine (i.e., fluorinating agent) into contact with 2-butanol to obtain 2-fluorobutane in a yield of 46%. Patent Literature 3 discloses that sec-butyl fluoride was produced by bringing sulfur hexafluoride into contact with a solution of sec-butyllithium in a cyclohexane/n-hexane mixture. Patent Literature 4 discloses that 2-fluorobutane was obtained by hydrogenating 2-fluorobutadiene in the presence of a catalyst. Non-Patent Literature 1 discloses a method that reacts acetyl fluoride (i.e., fluorinating agent) with an ether compound having a cyclic structure (e.g., adamantyl methyl ether or cyclohexyl methyl ether) using a boron trifluoride phosphoric acid complex or zinc fluoride as a catalyst to obtain a monofluorohydrocarbon.

CITATION LIST

Patent Literature

Patent Literature 1: WO02009-123038 (US20110068086A1)
Patent Literature 2: JP-A-59-46251
Patent Literature 3: JP-A-2009-292749
Patent Literature 4: U.S. Pat. No. 2,550,953

Non-Patent Literature

Non-Patent Literature 1: Bulletin of the Chemical Society of Japan, Vol. 41, 1724 (1968)

SUMMARY OF INVENTION

Technical Problem

The inventor reported a method for obtaining high-purity 2-fluorobutane (see WO02014/136877). However, it has been desired to relatively inexpensively produce 2-fluorobutane in high yield. Specifically, since the method disclosed in Patent Literature 2 has a problem in that the fluorinating agent used therefor is very expensive, and the method disclosed in Patent Literature 3 has a problem in that it is necessary to use an alkyllithium that may ignite, it is difficult to apply these methods from the viewpoint of industrial productivity.

The invention was conceived in view of the above situation. An object of the invention is to provide a method that can relatively safely and efficiently produce 2-fluorobutane.

Solution to Problem

The inventor effected a reaction according to the method disclosed in Non-Patent Literature 1 in the absence of a solvent, and found that a large amount of alkyl acetate (by-product) is produced in which the methyl group of the methyl alkyl ether is substituted with an acetyl group derived from the fluorination agent. The inventor conducted further extensive studies in order to reduce the amount of by-product. As a result, the inventor found that, when the reaction is effected in a hydrocarbon-based solvent, the reaction proceeds smoothly even at a low temperature, and it is possible to significantly reduce the amount of alkyl acetate produced as a by-product, and use a compound having a linear structure as the raw material (ether compound). This finding has led to the completion of the invention.

According to one aspect of the invention, a method for producing a fluorohydrocarbon represented by the following structural formula (3) includes bringing a secondary or tertiary ether compound represented by the following structural formula (1) into contact with an acid fluoride represented by the following structural formula (2) in a hydrocarbon-based solvent in the presence of a boron trifluoride complex,

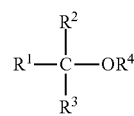

(1)

wherein each of $R^1$ and $R^2$ independently represents an alkyl group having 1 to 3 carbon atoms. $R^3$ represents a hydrogen atom, a methyl group, or an ethyl group, and $R^4$ represents a methyl group or an ethyl group, provided that $R^1$ and $R^2$ are optionally bonded to each other to form a ring structure,

(2)

wherein $R^5$ represents a methyl group or an ethyl group,

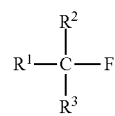

(3)

wherein $R^1$ to $R^3$ are the same as defined above.

It is preferable that the boron trifluoride complex be a boron trifluoride ether complex.

It is preferable that the secondary or tertiary ether compound represented by the structural formula (1) be sec-butyl methyl ether or t-butyl methyl ether.

It is preferable that the acid fluoride represented by the structural formula (2) be acetyl fluoride.

It is preferable that the fluorohydrocarbon represented by the structural formula (3) be 2-fluorobutane.

DESCRIPTION OF EMBODIMENTS

The exemplary embodiments of the invention are described in detail below.

A method according to one embodiment of the invention includes bringing a secondary or tertiary ether compound represented by the structural formula (1) into contact with an acid fluoride represented by the structural formula (2) in a hydrocarbon-based solvent in the presence of a boron trifluoride complex to produce a fluorohydrocarbon represented by the structural formula (3).

The starting material used in connection with one embodiment of the invention is the ether compound represented by the structural formula (1).

In the structural formula (1), each of $R^1$ and $R^2$ independently represents an alkyl group having 1 to 3 carbon atoms, $R^3$ represents a hydrogen atom, a methyl group, or an ethyl group, and $R^4$ represents a methyl group or an ethyl group.

It is preferable that the total number of carbon atoms included in $R^1$ to $R^4$ be 3 or 4.

Examples of the alkyl group having 1 to 3 carbon atoms that is represented by $R^1$ and $R^2$ include a methyl group, an ethyl group, an n-propyl group, and an isopropyl group.

$R^1$ and $R^2$ are optionally bonded to each other to form a ring structure. Note that it is preferable that $R^1$ and $R^2$ do not form a ring structure.

Examples of the ring structure formed when $R^1$ and $R^2$ are bonded to each other include a cyclopropane ring, a cyclobutane ring, a cyclopentane ring, a cyclohexane ring, a cycloheptane ring, and the like.

Specific examples of the ether compound represented by the structural formula (1) include a methyl ether such as sec-butyl methyl ether, t-butyl methyl ether, cyclobutyl methyl ether, 2-pentyl methyl ether, 3-pentyl methyl ether, 2-methyl-2-butyl methyl ether, and cyclopentyl methyl ether; an ethyl ether such as sec-butyl ethyl ether, t-butyl ethyl ether, cyclobutyl ethyl ether, 2-pentyl ethyl ether, 3-pentyl ethyl ether, 2-methyl-2-butyl ethyl ether, and cyclopentyl ethyl ether; and the like.

Among these, a methyl or ethyl ether that corresponds to an alcohol having 4 carbon atoms, such as sec-butyl methyl ether, t-butyl methyl ether, sec-butyl ethyl ether, and t-butyl ethyl ether, is preferable from the viewpoint of availability of the raw material.

These ether compounds may be produced using the method described in the Journal of the Japan Oil Chemist's Society, Vol. 31, p. 960 (1982), or the method described in the Journal of the American Chemical Society, Vol. 54, 2088 (1932), for example. The former method brings the corresponding alcohol into contact with a sulfuric ester in the presence of sodium hydroxide (concentration: 50%) and a phase transfer catalyst (e.g., tetraalkylammonium salt). The latter method brings the corresponding alcohol into contact with metallic sodium in an anhydrous state, and brings the resulting product into contact with an alkyl bromide or an alkyl iodide to produce an ether compound.

The above reaction is effected using the acid fluoride represented by the structural formula (2) as a fluorinating agent. The acid fluoride represented by the structural formula (2) is acetyl fluoride (acetic acid fluoride) or propionyl fluoride (propionic acid fluoride).

Acetyl fluoride and propionyl fluoride may be produced using the method described in the Journal of the Chemical Society, Dalton Transactions, 2129 (1975), or the method described in the Journal of the American Chemical Society, Vol. 59, 1474 (1937). The former method dissolves potassium fluoride in acetic acid, adds acetyl chloride or propionyl chloride to the solution with heating, and collects the resulting acetyl fluoride or propionyl fluoride. The latter method dissolve sodium hydrogen difluoride in acetic anhydride, adds acetyl chloride to the solution, and collects the resulting acetyl fluoride.

Acetyl fluoride or propionyl fluoride is preferably used in a ratio of 0.8 to 1.3 equivalents, and more preferably 0.9 to 1.2 equivalents, based on the ether compound used as the raw material. When acetyl fluoride or propionyl fluoride is used in a ratio within the above range, high productivity can be achieved, and the subsequent post-treatment and purification step can be simplified. Acetyl fluoride that has served as the fluorinating agent is converted into methyl acetate (when a methyl ether compound is used as the ether compound) or ethyl acetate (when an ethyl ether compound is used as the ether compound). When propionyl fluoride is used as the fluorinating agent, propionyl fluoride is converted into methyl propionate or ethyl propionate.

The hydrocarbon-based solvent used in connection with one embodiment of the invention is preferably a compound having a boiling point higher than that of the fluorohydrocarbon (i.e., product) by 25° C. or more taking account of the load during the subsequent purification step (purification by distillation). Specific examples of the hydrocarbon-based solvent include a hydrocarbon having 5 carbon atoms, such as n-pentane and cyclopentane; a hydrocarbon having 6 carbon atoms, such as n-hexane, 2-methylpentane, 3-methylpentane, 2,2-dimethylbutane, 2,3-dimethylbutane, cyclohexane, and methylcyclopentane; a hydrocarbon having 7 carbon atoms, such as n-heptane, 2-methylhexane, 3-methylhexane, 2,2-dimethylpentane, 2,3-dimethylpentane, 2,4-dimethylpentane, 3,3-dimethylpentane, 3-ethyl pentane, 2,2,3-trimethylbutane, methylcyclohexane, cycloheptane, and toluene; a hydrocarbon having 8 carbon atoms, such as n-octane, 4-methylheptane, 2-methylheptane, 3-methylheptane, 2,2-dimethylhexane, 2,3-dimethylhexane, 2,4-dimethylhexane, 2,5-dimethylhexane, 3,3-dimethylhexane, 3,4-dimethylhexane, 3-ethylhexane, 2,2,3-trimethylpentane, 2,2,4-trimethylpentane, 2,3,3-trimethylpentane, 2,3,4-trimethylpentane, 2-methyl-3-ethylpentane, 3-methyl-3-ethylpentane, cyclooctane, ethylbenzene, and xylene; and the like. A mixture including isomers of a hydrocarbon may also be used as the hydrocarbon-based solvent.

Among these, a hydrocarbon having 6 carbon atoms, such as n-hexane, 2-methylpentane, 3-methylpentane, 2,2-dimethylbutane, 2,3-dimethylbutane, cyclohexane, and methylcyclopentane, and a hydrocarbon having 7 carbon atoms, such as n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, methylcyclohexane, cycloheptane, and toluene, are preferable from the viewpoint of ease of handling.

The hydrocarbon-based solvent is normally used in an amount of 2.5 to 3 ml based on 1 g of the ether compound used as the raw material.

If the hydrocarbon-based solvent is used in too small an amount, a large amount of alkyl acetate (i.e., by-product) may be produced. If the hydrocarbon-based solvent is used in too large an amount, it may take time to complete the reaction, or a complex waste treatment may be required.

The method according to one embodiment of the invention uses the boron trifluoride complex as a catalyst. Specific examples of the boron trifluoride complex include a boron trifluoride acetic acid complex, a boron trifluoride acetonitrile complex, a boron trifluoride ethylamine complex, a boron trifluoride methanol complex, a boron trifluoride propanol complex, a boron trifluoride dimethyl sulfide complex, a boron trifluoride phosphoric acid complex, a boron trifluoride dimethyl ether complex, a boron trifluoride diethyl ether complex, a boron trifluoride t-butyl methyl ether complex, a boron trifluoride dibutyl ether complex, a boron trifluoride tetrahydrofuran complex, and the like. Among these, a boron trifluoride ether compound complex (e.g., boron trifluoride dimethyl ether complex, boron trifluoride diethyl ether complex, boron trifluoride t-butyl methyl ether complex, boron trifluoride dibutyl ether complex, and boron trifluoride tetrahydrofuran complex) is preferable, and a boron trifluoride diethyl ether complex and a boron trifluoride tetrahydrofuran complex are more preferable from the viewpoint of ease of handling.

The boron trifluoride complex is used in a ratio of 0.01 to 10 mol %, and preferably 0.1 to 5 mol %, based on the secondary or tertiary ether compound that is used as the raw material. If the boron trifluoride complex is used in too small a ratio, a significant decrease in reaction rate may occur. If the boron trifluoride complex is used in too large a ratio, the viscosity of the resulting mixture may increase, and it may be difficult to stir the mixture, or the reaction may proceed rapidly, whereby bumping may occur.

The reaction temperature is preferably set to −30 to +30° C., and more preferably −10 to +20° C. When the reaction temperature is within the above range, an appropriate reaction rate and high productivity can be achieved. Moreover, it is possible to suppress loss of the fluorohydrocarbon (product) due to volatilization.

The reaction time is selected taking account of a combination of the ether compound (raw material), the acid fluoride, and the hydrocarbon-based solvent, but is normally 0.5 to 10 hours, and preferably 1 to 5 hours. When the reaction time is within the above range, the reaction proceeds sufficiently, and it is possible to reduce the amount of unreacted raw material and residual acid fluoride. Moreover, it is possible to suppress the production of by-products due to an excessive reaction.

When effecting the reaction, a reactor is charged with the ether compound (raw material), the acid fluoride (fluorinating agent), and the hydrocarbon-based solvent, and the temperature of the reactor is adjusted to a specific temperature (−30 to 0° C.). The boron trifluoride complex (catalyst) is then added to the mixture at one time. The mixture is then stirred while maintaining the mixture at a specific temperature (i.e., an arbitrary temperature within the range from −30° C. to +30° C.).

A post-treatment (i.e., a treatment after completion of the reaction) may be performed using an ordinary method. For example, water or a weak alkali is added to the reaction mixture that has been sufficiently cooled (about 0° C.) to inactivate and hydrolyze the boron trifluoride complex and unreacted acid fluoride, and the organic layer is isolated preparatively, and dried. The organic layer (solution) is then rectified to isolate the fluorohydrocarbon (target product). Rectification may be repeated when it is desired to further increase the purity of the fluorohydrocarbon.

The fluorohydrocarbon represented by the structural formula (3) can thus be obtained.

Specific examples of the fluorohydrocarbon represented by the structural formula (3) include 2-fluorobutane, t-butyl fluoride, 2-fluoropentane, 3-fluoropentane, 2-methyl-2-fluorobutane, cyclobutyl fluoride, cyclopentyl fluoride, cyclohexyl fluoride, and the like.

Among these, 2-fluorobutane and t-butyl fluoride are preferable from the viewpoint of availability of the raw material.

EXAMPLES

The invention is further described below by way of examples. Note that the scope of the invention is not limited to the following examples. The unit "%" refers to "wt %" unless otherwise indicated.

The analysis conditions employed in connection with the examples are described below.
(1) Gas chromatography analysis (GC analysis)
Device: HP-6890 manufactured by Agilent Technologies
Column: Inert Cap-1 manufactured by GL Sciences Inc. (length: 60 m, inner diameter 0.25 mm, thickness: 1.5 μm)
Column temperature: The column was held at 40° C. for 10 minutes, heated at 20° C./min, and held at 40° C. for 10 minutes.
Injection temperature: 200° C.
Carrier gas: nitrogen
Split ratio: 100/1
Detector: FID
(2) Gas chromatography-mass spectrometry
GC device: HP-6890 manufactured by Agilent Technologies
Column: Inert Cap-1 manufactured by GL Sciences Inc. (length: 60 m, inner diameter 0.25 mm, thickness: 1.5 μm)
Column temperature: The column was held at 40° C. for 10 minutes, heated at 20° C./min, and held at 240° C. for 10 minutes.
MS device: 5973 NETWORK manufactured by Agilent Technologies
Detector: EI (accelerating voltage: 70 eV)

Production Example 1: Production of Sec-Butyl Methyl Ether

A 500 ml recovery flask charged with a stirring bar, was charged with 360 ml of 2-butanol and 37.3 g of flaky potassium hydroxide (manufactured by Aldrich, purity: about 90%), and the mixture was stirred at 50° C. for 2.5 hours. Heating was stopped when a homogeneous solution had been obtained through the dissolution of potassium hydroxide. After the addition of 84.4 g of iodomethane to the homogeneous solution, the mixture was vigorously stirred at 50° C. for 3 hours in a state in which a Dimroth condenser was provided. The recovery flask (reaction vessel) was cooled to room temperature (about 25° C.), and the supernatant liquid was analyzed by gas chromatography. It was found that iodomethane had been almost completely consumed, and the supernatant liquid was a mixture including 2-methoxybutane (target product) and 2-butanol. The mixture contained in the recovery flask was filtered to remove potassium iodide. The potassium iodide thus removed was dissolved in a small quantity of water, and the upper-layer organic phase was separated, and mixed with the filtrate to obtain a filtrate mixture.

A still was charged with the filtrate mixture, and a distillation operation was performed using a KS rectifying column (manufactured by Toka Seiki Co., Ltd., column length: 30 cm, packing material: Heli Pack No. 1). A fraction from the top of the column (temperature: 55 to 56° C.) was collected, followed by separation of azeotropic water using a separating funnel, and the product was dried using a molecular sieve 4A to obtain 38 g of sec-butyl methyl ether (yield: 72%).

GC-MS (EI-MS): m/z 73, 59, 41, 29

Production Example 2: Production of Sec-Butyl Ethyl Ether

A 500 ml recovery flask charged with a stirring bar, was charged with 240 ml of 2-butanol and 24.8 g of flaky potassium hydroxide (manufactured by Aldrich, purity: about 90%), and the mixture was stirred at 50° C. for 3 hours. Heating was stopped when a homogeneous solution had been obtained through the dissolution of potassium hydroxide. After the addition of 43 g of ethyl bromide to the homogeneous solution, the mixture was vigorously stirred at 70° C. for 4 hours in a state in which a Dimroth condenser was provided. The recovery flask (reaction vessel) was cooled to room temperature (about 25° C.), and the supernatant liquid was analyzed by gas chromatography. It was found that ethyl bromide had been almost completely consumed, and the supernatant liquid was a mixture including 2-ethoxybutane (target product) and 2-butanol. The mixture contained in the recovery flask was filtered to remove potassium bromide. The potassium bromide thus removed was dissolved in a small quantity of water, and the upper-layer organic phase was separated, and mixed with the filtrate to obtain a filtrate mixture.

A still was charged with the filtrate mixture, and a distillation operation was performed using a KS rectifying column (manufactured by Toka Seiki Co., Ltd., column length: 30 cm, packing material: Heli Pack No. 1). A fraction from the top of the column (temperature: 68 to 69° C.) was collected, followed by separation of azeotropic water using a separating funnel, and the product was dried using a molecular sieve 4A to obtain 31 g of sec-butyl ethyl ether (yield: 51%).

GC-MS (EI-MS): m/z 87, 73, 59, 45

Production Example 3: Production of Acetyl Fluoride (Acetic Acid Fluoride)

A 500 ml glass reactor equipped with a stirrer, a dropping funnel, and a trap was charged with 200 ml of acetic anhydride and 46.9 g of potassium hydrogen difluoride, and the mixture was heated to 40° C. with stirring.

After the dropwise addition of 47 g of acetyl chloride to the mixture from the dropping funnel over 40 minutes, the internal temperature of the reactor was increased at 10° C./15 min.

When the internal temperature of the reactor had reached 90° C. the mixture was heated at 90° C. for 20 minutes, and the reaction was terminated. Acetyl fluoride that distilled from the reactor during the above operation was collected into the trap (glass trap) cooled with ice water. 47.6 g of crude acetyl fluoride was thus obtained (yield: 128%). Note that the yield exceeds 100% since acetyl fluoride is also produced from acetic anhydride.

The resulting crude acetyl fluoride was subjected to simple distillation to collect a fraction from the top of the column (temperature: 20 to 24° C.). 42.4 g of acetyl fluoride was thus obtained (yield: 114%).

Production Example 4: Production of Propionyl Fluoride (Propionic Acid Fluoride)

A 500 ml glass reactor equipped with a stirrer, a dropping funnel, and a trap was charged with 200 ml of propionic anhydride and 46.8 g of potassium hydrogen difluoride, and the mixture was heated to 90° C. with stirring.

After the dropwise addition of 55.5 g of propionyl chloride to the mixture from the dropping funnel over 1 hour, the resulting mixture was stirred for 15 minutes. After heating the reactor to 110° C. at 10° C./15 min, the mixture was heated at 110° C. for 30 minutes, and the reaction was terminated. Propionyl fluoride that distilled from the reactor during the above operation was collected into the trap (glass trap) cooled with ice water. The yield of crude propionyl fluoride was 132%.

The resulting crude propionyl fluoride was subjected to simple distillation to collect a fraction from the top of the column (temperature: 42 to 43° C.). 46.8 g of propionyl fluoride was thus obtained (yield: 103%).

Example 1

A 50 ml glass reactor equipped with a stirrer and a Dimroth condenser was charged with 3.52 g of sec-butyl methyl ether synthesized in Production Example 1, 2.98 g of acetyl fluoride synthesized in Production Example 3, and 10 ml of n-hexane, and the mixture was cooled to 0° C., and stirred. After the addition of 0.28 g of a boron trifluoride tetrahydrofuran complex to the mixture using a syringe, the resulting mixture was stirred at 0° C. for 3 hours. The mixture was then analyzed by gas chromatography. It was found that sec-butyl methyl ether used as the raw material had almost completely disappeared, and the mixture included 24.45% by area of 2-fluorobutane (i.e., target product), 0.18% by area of 1-butene, 6.50% by area of (E)-2-butene, and 2.00% by area of (Z)-2-butene. It was also found that the mixture included only 0.35% by area of 2-acetoxybutane (that was produced by acetoxylation of the raw material). Note that the balance of the mixture consisted of n-hexane (that was used as the solvent), tetrahydrofuran (derived from the complex), and methyl acetate.

Example 2

A reaction was effected in the same manner as in Example 1, except that the amount of acetyl fluoride was changed to 2.23 g. After effecting the reaction for 3 hours, the resulting mixture was analyzed by gas chromatography. It was found that acetyl fluoride used as the fluorinating agent had almost completely disappeared, and the mixture included 18.92% by area of 2-fluorobutane (i.e., target product), 0.13% by area of 1-butene, 4.56% by area of (E)-2-butene, 1.55% by area of (Z)-2-butene, and 3.84% by area of sec-butyl methyl ether used as the raw material. It was also found that the mixture included only 0.25% by area of 2-acetoxybutane (that was produced by acetoxylation of the raw material).

Example 3

A reaction was effected in the same manner as in Example 1, except that 0.23 g of a boron trifluoride dimethyl ether complex was used instead of 0.28 g of the boron trifluoride tetrahydrofuran complex. After effecting the reaction for 3 hours, the resulting mixture was analyzed by gas chromatography. It was found that sec-butyl methyl ether used as the raw material had almost completely disappeared, and the mixture included 20.24% by area of 2-fluorobutane (i.e., target product), 0.19% by area of 1-butene, 6.07% by area of (E)-2-butene, and 2.43% by area of (Z)-2-butene. It was also found that the mixture included only 0.16% by area of 2-acetoxybutane (that was produced by acetoxylation of the raw material).

Example 4

A reaction was effected in the same manner as in Example 1, except that 0.26 g of a boron trifluoride diethyl ether complex was used instead of 0.28 g of the boron trifluoride tetrahydrofuran complex. After effecting the reaction for 3 hours, the resulting mixture was analyzed by gas chromatography. It was found that sec-butyl methyl ether used as the raw material had almost completely disappeared, and the mixture included 20.00% by area of 2-fluorobutane (i.e., target product), 0.18% by area of 1-butene, 6.36% by area of (E)-2-butene, and 2.59% by area of (Z)-2-butene. It was also found that the mixture included only 0.44% by area of 2-acetoxybutane (that was produced by acetoxylation of the raw material).

Example 5

A reaction was effected in the same manner as in Example 1, except that 0.31 g of a boron trifluoride t-butyl methyl ether complex was used instead of 0.28 g of the boron trifluoride tetrahydrofuran complex. After effecting the reaction for 3 hours, the resulting mixture was analyzed by gas chromatography. It was found that sec-butyl methyl ether used as the raw material had almost completely disappeared, and the mixture included 21.07% by area of 2-fluorobutane (i.e., target product), 0.22% by area of 1-butene, 7.28% by area of (E)-2-butene, and 3.10% by area of (Z)-2-butene. It was also found that the mixture included only 0.66% by area of 2-acetoxybutane (that was produced by acetoxylation of the raw material).

Example 6

A reaction was effected in the same manner as in Example 1, except that 10 ml of cyclohexane was used as the solvent instead of 10 ml of n-hexane. After effecting the reaction for 3 hours, the resulting mixture was analyzed by gas chromatography. It was found that sec-butyl methyl ether used as the raw material had almost completely disappeared, and the mixture included 21.18% by area of 2-fluorobutane (i.e., target product), 0.170/% by area of 1-butene, 6.15% by area of (E)-2-butene, and 1.85% by area of (Z)-2-butene. It was also found that the mixture included only 0.10% by area of 2-acetoxybutane (that was produced by acetoxylation of the raw material).

Example 7

A reaction was effected in the same manner as in Example 1, except that 10 ml of heptane was used as the solvent instead of 10 ml of n-hexane. After effecting the reaction for 3 hours, the resulting mixture was analyzed by gas chromatography. It was found that sec-butyl methyl ether used as the raw material had almost completely disappeared, and the mixture included 22.48% by area of 2-fluorobutane (i.e., target product), 0.17% by area of 1-butene, 5.98% by area of (E)-2-butene, and 1.91% by area of (Z)-2-butene. It was also found that the mixture included only 0.48% by area of 2-acetoxybutane (that was produced by acetoxylation of the raw material).

Example 8

A reaction was effected in the same manner as in Example 1, except that 10 ml of toluene was used as the solvent instead of 10 ml of n-hexane. After effecting the reaction for 3 hours, the resulting mixture was analyzed by gas chromatography. It was found that the mixture included 9.78% by area of 2-fluorobutane (i.e., target product), 0.19% by area of 1-butene, 4.41% by area of (E)-2-butene, 1.10% by area of (Z)-2-butene, and 8.00% by area of sec-butyl methyl ether used as the raw material. It was also found that the mixture included only 0.34% by area of 2-acetoxybutane (that was produced by acetoxylation of the raw material).

Example 9

A reaction was effected in the same manner as in Example 1, except that 4.08 g of sec-butyl ethyl ether synthesized in Production Example 2 was used as the raw material instead of 3.52 g of sec-butyl methyl ether. After effecting the reaction for 3 hours, the resulting mixture was analyzed by gas chromatography. It was found that sec-butyl ethyl ether used as the raw material had almost completely disappeared, and the mixture included 18.66% by area of 2-fluorobutane (i.e., target product), 0.11% by area of 1-butene, 4.68% by area of (E)-2-butene, and 1.24% by area of (Z)-2-butene. It was also found that the mixture included only 0.82% by area of 2-acetoxybutane (that was produced by acetoxylation of the raw material).

Example 10

A reaction was effected in the same manner as in Example 1, except that 4.08 g of sec-butyl ethyl ether synthesized in Production Example 2 was used as the raw material instead of 3.52 g of sec-butyl methyl ether, and 10 ml of cyclohexane was used as the solvent instead of 10 ml of n-hexane. After effecting the reaction for 3 hours, the resulting mixture was analyzed by gas chromatography. It was found that sec-butyl ethyl ether used as the raw material had almost completely disappeared, and the mixture included 18.00% by area of 2-fluorobutane (i.e., target product), 0.11% by area of 1-butene, 4.62% by area of (E)-2-butene, and 1.24% by area of (Z)-2-butene. It was also found that the mixture included only 0.87% by area of 2-acetoxybutane (that was produced by acetoxylation of the raw material).

Example 11

A reaction was effected in the same manner as in Example 1, except that 3.53 g of t-butyl methyl ether (manufactured by Wako Pure Chemical Industries, Ltd.) was used as the raw material instead of 3.52 g of sec-butyl methyl ether. After effecting the reaction for 3 hours, the resulting mixture was analyzed by gas chromatography. It was found that t-butyl methyl ether used as the raw material had almost completely disappeared, and the mixture included 17.69% by area of t-butyl fluoride (i.e., target product) and 2.52% by area of isobutene. It was also found that the mixture included only 0.72% by area of a product produced by acetoxylation of the raw material.

Example 12

A reaction was effected in the same manner as in Example 1, except that 4.02 g of t-butyl ethyl ether (manufactured by Tokyo Chemical Industry Co., Ltd.) was used as the raw material instead of 3.52 g of sec-butyl methyl ether. After effecting the reaction for 3 hours, the resulting mixture was analyzed by gas chromatography. It was found that t-butyl ethyl ether used as the raw material had almost completely disappeared, and the mixture included 19.10% by area of t-butyl fluoride (i.e., target product) and 1.10% by area of isobutene. It was also found that the mixture included only 0.095% by area of a product produced by acetoxylation of the raw material.

Example 13

A reaction was effected in the same manner as in Example 1, except that 3.65 g of propionyl fluoride synthesized in Production Example 4 was used as the fluorinating agent instead of 2.98 g of acetyl fluoride. After effecting the reaction for 3 hours, the resulting mixture was analyzed by gas chromatography. It was found that sec-butyl methyl ether used as the raw material had almost completely disappeared, and the mixture included 20.06% by area of 2-fluorobutane (i.e., target product), 0.16% by area of 1-butene, 2.03% by area of (E)-2-butene, and 1.69% by area of (Z)-2-butene. It was also found that the mixture included only 0.55% by area of 2-propionyloxybutane (that was produced by propionyloxylation of the raw material).

Example 14

A reaction was effected in the same manner as in Example 8, except that 3.65 g of propionyl fluoride synthesized in Production Example 4 was used as the fluorinating agent instead of acetyl fluoride. After effecting the reaction for 7 hours, the resulting mixture was analyzed by gas chromatography. It was found that sec-butyl methyl ether used as the raw material had almost completely disappeared, and the mixture included 17.43% by area of 2-fluorobutane (i.e., target product), 0.14% by area of 1-butene, 6.65% by area of (E)-2-butene, and 1.91% by area of (Z)-2-butene. It was also found that the mixture included only 1.30% by area of 2-propionyloxybutane (that was produced by propionyloxylation of the raw material).

Example 15

A reaction was effected in the same manner as in Example 11, except that 3.65 g of propionyl fluoride synthesized in Production Example 4 was used as the fluorinating agent instead of acetyl fluoride. After effecting the reaction for 3 hours, the resulting mixture was analyzed by gas chromatography. It was found that t-butyl methyl ether used as the raw material had almost completely disappeared, and the mixture included 19.96% by area of t-butyl fluoride (i.e., target product) and 4.01% by area of isobutene. It was also found that the mixture included only 0.24% by area of a product produced by propionyloxylation of the raw material.

Comparative Example 1

A reaction was effected in the same manner as in Example 1, except that n-hexane (solvent) was not added. After effecting the reaction for 3 hours, 10 ml of n-hexane was added to the reactor, and the resulting mixture was analyzed by gas chromatography. It was found that sec-butyl methyl ether used as the raw material had almost completely disappeared, and the mixture included 12.20% by area of 2-fluorobutane (i.e., target product), 0.24% by area of 1-butene, 6.32% by area of (E)-2-butene, and 2.64% by area of (Z)-2-butene. It was also found that the mixture included 9.24% by area of 2-acetoxybutane (that was produced by acetoxylation of the raw material).

Comparative Example 2

A reaction was effected in the same manner as in Example 1, except that 10 ml of 2-pentanone was used as the solvent instead of 10 ml of n-hexane. After effecting the reaction for 3 hours, the resulting mixture was analyzed by gas chromatography. It was found that the mixture included 10.79% by area of 2-fluorobutane (i.e., target product), 0.28% by area of 1-butene, 5.87% by area of (E)-2-butene, 1.59% by area of (Z)-2-butene, and 10.79% by area of sec-butyl methyl ether used as the raw material. It was also found that the mixture included 4.01% by area of 2-acetoxybutane (that was produced by acetoxylation of the raw material), and 7.01% by area of a high-boiling-point component of which the structure has not been identified.

Comparative Example 3

A reaction was effected in the same manner as in Example 1, except that 10 ml of ethyl acetate was used as the solvent instead of 10 ml of n-hexane. After effecting the reaction for 3 hours, the resulting mixture was analyzed by gas chromatography. It was found that the mixture included 14.56% by area of 2-fluorobutane (i.e., target product), 0.25% by area of 1-butene, 10.03% by area of (E)-2-butene, 2.47% by area of (Z)-2-butene, and 7.51% by area of sec-butyl methyl ether used as the raw material. It was also found that the mixture included 0.24% by area of 2-acetoxybutane (that was produced by acetoxylation of the raw material).

These results suggest that the reaction rate is low, and a large amount of raw material remains when a ketone-based solvent or an ester-based solvent is used as compared with the case where a hydrocarbon-based solvent is used.

The invention claimed is:
1. A method for producing a fluorohydrocarbon of formula (3) comprising bringing a secondary or tertiary ether compound of formula (1) into contact with an acid fluoride of formula (2) in a hydrocarbon-based solvent in the presence of a boron trifluoride complex,

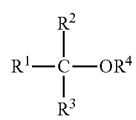

(1)

wherein each of $R^1$ and $R^2$ independently represents an alkyl group having 1 to 3 carbon atoms, $R^3$ represents a hydrogen atom, a methyl group, or an ethyl group, and $R^4$ represents a methyl group or an ethyl group, provided that $R^1$ and $R^2$ are optionally bonded to each other to form a ring structure,

(2)

wherein $R^5$ represents a methyl group or an ethyl group,

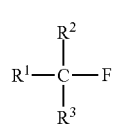

(3)

wherein $R^1$ to $R^3$ are the same as defined above.

2. The method according to claim 1, wherein the boron trifluoride complex is a boron trifluoride ether complex.

3. The method according to claim 1, wherein the secondary or tertiary ether compound of formula (1) is sec-butyl methyl ether or t-butyl methyl ether.

4. The method according to claim 1, wherein the acid fluoride of formula (2) is acetyl fluoride.

5. The method according to claim 1, wherein the fluorohydrocarbon of formula (3) is 2-fluorobutane.

\* \* \* \* \*